(12) United States Patent
Obee et al.

(10) Patent No.: US 7,112,306 B2
(45) Date of Patent: Sep. 26, 2006

(54) ELECTRODELESS ULTRAVIOLET DISCHARGE FLUID REMEDIATION

(75) Inventors: Timothy N. Obee, South Windsor, CT (US); Stephen O. Hay, South Windsor, CT (US); Joseph J. Sangiovanni, West Suffield, CT (US); Jared B. Hertzberg, New Haven, CT (US)

(73) Assignee: Carrier Corporation, Farmington, CT (US)

(*) Notice: Subject to any disclaimer, the term of this patent is extended or adjusted under 35 U.S.C. 154(b) by 703 days.

(21) Appl. No.: 10/140,082

(22) Filed: May 6, 2002

(65) Prior Publication Data

US 2003/0206833 A1 Nov. 6, 2003

(51) Int. Cl.
*A61L 2/10* (2006.01)
*A61L 2/12* (2006.01)
*B01J 19/12* (2006.01)

(52) U.S. Cl. .................... 422/121; 422/122; 422/186.3
(58) Field of Classification Search .................... 422/4, 422/21, 24, 121, 122, 186.3
See application file for complete search history.

(56) References Cited

U.S. PATENT DOCUMENTS

| | | | | |
|---|---|---|---|---|
| 4,532,427 A | * | 7/1985 | Matthews et al. | 250/492.2 |
| 5,564,065 A | * | 10/1996 | Fleck et al. | 422/186.3 |
| 5,614,151 A | | 3/1997 | LeVay et al. | |
| 5,790,934 A | | 8/1998 | Say et al. | |
| 5,817,276 A | | 10/1998 | Fencl et al. | |
| 5,865,959 A | | 2/1999 | Meinzer et al. | |
| 5,866,076 A | | 2/1999 | Fencl et al. | |
| 6,267,924 B1 | | 7/2001 | Fencl et al. | |

FOREIGN PATENT DOCUMENTS

| | | | | |
|---|---|---|---|---|
| JP | 61096649 A | * | 5/1986 |
| JP | 09253451 A | * | 9/1997 |
| JP | 2000223081 A | * | 8/2000 |
| WO | WO 9511751 A1 | * | 5/1995 |
| WO | WO 01/09924 A1 | | 2/2001 |

* cited by examiner

Primary Examiner—William H. Beisner
(74) Attorney, Agent, or Firm—M. P. Williams

(57) ABSTRACT

Spherical (23) or cylindrical (27, 36) electrodeless ultraviolet lamps are used to remediate fluid, directly or by excitation of ultraviolet-activated photocatalyst surfaces, which may be on the lamps themselves, or on structures which are permeable by the fluid. The lamps may be excited in cavities (18, 19; 43) by microwave energy from a magnetron (22), or by radio frequency power (39) inductively coupled (40) to the lamps. The lamps (44) may have start-up electrodes (47).

7 Claims, 2 Drawing Sheets

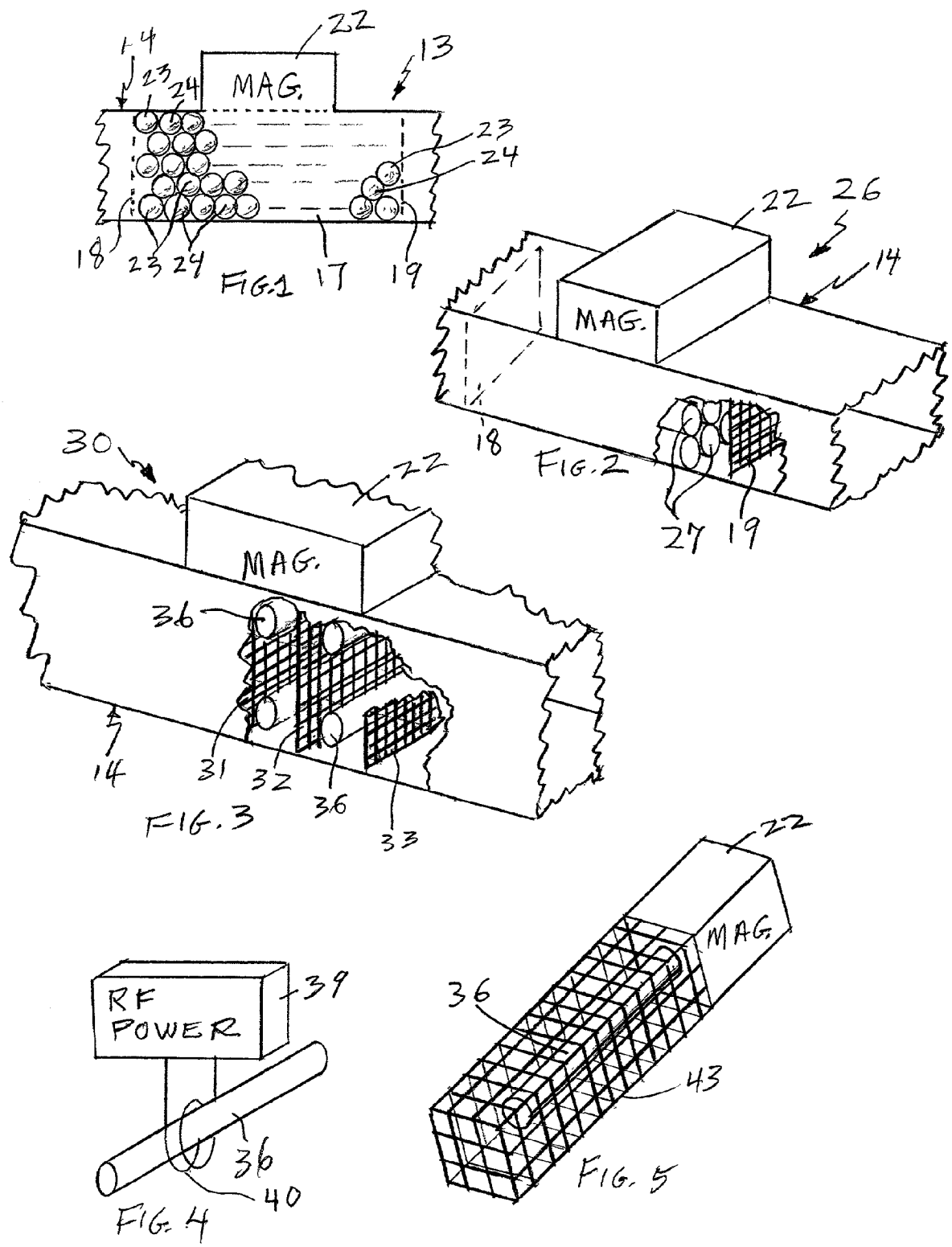

ELECTRODELESS ULTRAVIOLET DISCHARGE FLUID REMEDIATION

TECHNICAL FIELD

This invention relates to remediation of fluids in a finite space by means of ultraviolet radiation from electrodeless ultraviolet discharge devices, including the excitation of photocatalytic surfaces to promote chemical reactions.

BACKGROUND ART

Typical air purifiers use electrode discharge ultraviolet lamps; in some cases, the ultraviolet light is relied upon to wholly or partially destroy microorganisms; in other cases, the ultraviolet light activates a photocatalyst on the surface of a packed bed of pellets or of a structure which is permeable by the air flowing therethrough. Similar apparatus may be used in chemical processes in which photocatalytic oxidation of air or water streams is performed either to remediate (i.e., sterilize) or otherwise condition the stream.

Because of the short lamp life, air-purifier designs must be made suitable for lamp changeover. Such designs are unnecessarily large in volume, require a large number of ultraviolet lamps and photocatalyst elements (when used). The efficiency of electrode ultraviolet lamps (such as mercury lamps) is less than 30%; that is, less than 30% of the electrical input is converted to ultraviolet radiation. Lamps of this sort are utilized in U.S. Pat. No. 6,280,686 and patents referred to therein.

Consider, as an example, current, standard practice employed in commercial photocatalytic treatment of process streams, such as air-purification of contaminated air in occupied space of buildings. An effective design requires the bringing together, in space and time, of the ultraviolet photon, the photocatalyst surface element, and the process stream (e.g., the contaminants in the air in the air-purification example). Present design practice fixes the photocatalyst in space and places the ultraviolet irradiating source externally to the photocatalyst. Consequently, photocatalyst surface elements are rendered non-uniformly irradiated, dimly irradiated, and non-irradiated. This practice necessarily imposes a limit on the degrees of freedom available to the design.

As an illustrative application example, present commercial photocatalytic air purifiers all use electrode discharge ultraviolet lamps and a photocatalyst element that is configured as a packed bed of photocatalyst pellets or as a porous monolith support (i.e., honeycomb, reticulate foam, screen, woven or unwoven fiber, etc.) having a photocatalyst coating. The primary deficiencies of this design are twofold: First, because the source of ultraviolet radiation is external to the photocatalyst support and photocatalyst surface, that is, the source of ultraviolet radiation and the photocatalyst surface are necessarily separate in space, the illumination is inherently non-uniform, which results in dimly irradiated or non-irradiated surface elements, and consequently poor contaminant destruction. Because of this inherent deficiency, the design objective of delivery of the ultraviolet photons to the photocatalyst, while simultaneously achieving delivery of the contaminant (process stream) to a suitably activated photocatalyst, creates a difficult design problem. Second, fluid processing apparatus has heretofore been limited by the use of ultraviolet lamps which rely on an electric discharge between electrodes in order to sustain the creation of ultraviolet radiation. These devices suffer from the deposit of impurities resulting from heat concentration at the electrodes, which in turn inhibits electron emission and, therefore, UV photo emission. Lamp irradiation diminishes with time as the lamp ages and results in a useful lamp life that is less than about 8,000 hours; an inherent characteristic of electrode based ultraviolet lamps. These deficiencies result in air-purifier designs that are large in volume, require a large number of ultraviolet lamps and photocatalyst elements, and consume a large amount of electrical power. Although the air-purification example is used to illustrate shortcomings of external irradiation, those same deficiencies are inherent in all applications that have the ultraviolet radiation sources external to the photocatalyst.

DISCLOSURE OF INVENTION

As used herein, "remediation" encompasses photocatalytic and photochemical processes, and includes (1) "decontamination" which means (a) (i) to wholly or (ii) partially (b) (i) destroy, (ii) kill or (iii) vaporize any microorganism, and (2) "decomposition", which means oxidation or reduction of compounds.

Objects of the invention include: fluid remediation utilizing ultraviolet radiation having lamp life exceeding ten years; ultraviolet fluid remediation having highly efficient utilization of electrical input energy, such as on the order of 80% efficiency; fluid remediation which can be performed in relatively compact space; highly efficient photocatalytic fluid remediation; photocatalytic fluid remediation which is easily implemented in an energy efficient manner; and improved ultraviolet and photocatalytic fluid remediation.

According to the present invention, electrodeless ultraviolet lamps are used in a fluid remediation zone. The ultraviolet lamps may be used alone or in conjunction with ultraviolet-activated photocatalyst surfaces in the space. The lamps may be activated by microwaves provided by a magnetron, in groups, or individually. The lamps may be activated by inductively coupled radio frequency power. Photocatalytic surfaces may be on the lamps, or on particles of photocatalyst or non-photocatalyst elements. The lamps may be spheres or cylinders. The fluid being treated may be air, water or other fluids.

Furthermore, this invention relates to photocatalytic and photochemical processing for processing oxidation or reduction reactions. Possible applications for this invention are varied, for example, air-purification of occupied spaces (e.g., residential and commercial buildings, transportation vehicles, etc.), ethylene control in transportation of horticultural commodities, remediation of contaminated soil and water, and generally for any contaminated air or water stream, for chemical synthesis, and for microbial sterilization. The key feature of this aspect of the invention is the intimate integration of UV light and photocatalyst surfaces, which allows increased freedom to independently control UV intensity and fluid phase mass transport processes. The present invention provides a long-lived source of ultraviolet emission as well as compact and highly efficient photocatalytic reactors for air purification and other applications. The present invention brings the ultraviolet source and the photocatalyst surface into intimate proximity, thereby achieving nearly uniform irradiation of all photocatalytic surface elements. This intimate integration of ultraviolet irradiating source and photocatalytic surface greatly improves the freedom to independently control ultraviolet intensity and transport processes, that is, transport of chemical reactants in the process stream to the photocatalyst surface.

The invention provides fluid remediation having ultraviolet lamps with lives exceeding ten years, thereby simplifying the apparatus and reducing the cost of maintenance significantly. The invention provides ultraviolet efficiency on the order of 80%, including power transfer losses by the radio or microwave generators and cavities.

Other objects, features and advantages of the present invention will become more apparent in the light of the following detailed description of exemplary embodiments thereof, as illustrated in the accompanying drawings.

BRIEF DESCRIPTION OF THE DRAWINGS

FIG. 1 is a simplified, stylized side schematic view of a duct having spheres including electrodeless ultraviolet lamps in a magnetron-activated microwave cavity.

FIG. 2 is a partially broken away, simplified schematic perspective view of cylindrical electrodeless ultraviolet lamps disposed in a magnetron-activated microwave cavity within a duct.

FIG. 3 is a partially broken away, stylized schematic perspective view of cylindrical electrodeless ultraviolet lamps disposed between photocatalytic-coated fluid-permeable substrates.

FIG. 4 is a simplified, schematic perspective view of a cylindrical electrodeless ultraviolet lamp being inductively excited by radio frequency power.

FIG. 5 is a simplified, schematic perspective view of a tubular electrodeless ultraviolet lamp disposed within a magnetron-energized microwave cavity.

MODE(S) FOR CARRYING OUT THE INVENTION

Figure 6:
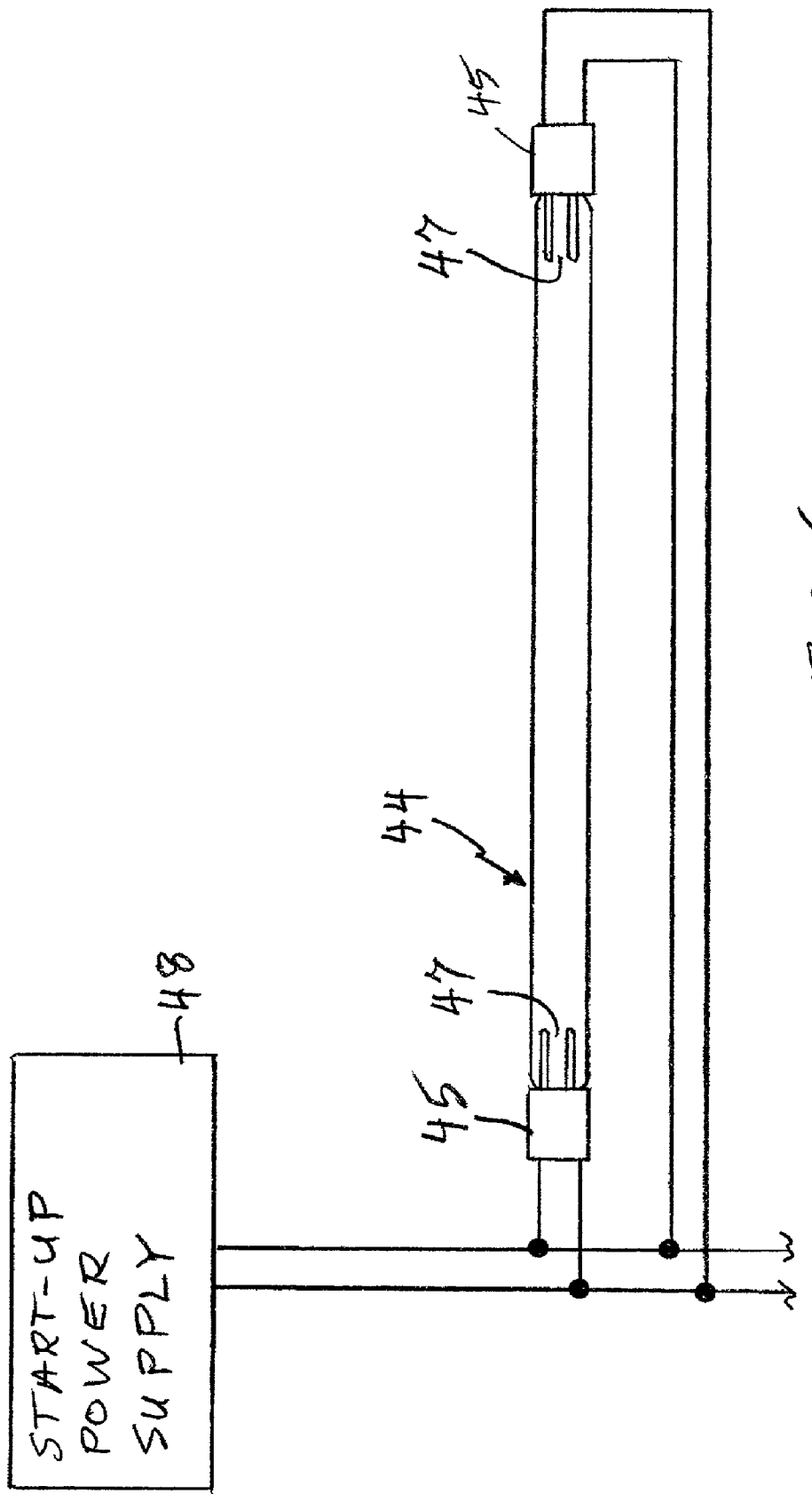
FIG. 6 is a simplified, schematic side elevation view of a tubular electrodeless ultraviolet lamp having starter electrodes and power supply.

In FIG. 1, a fluid remediation zone 13 is formed within a duct 14 which comprises microwave reflecting material. At each end of a finite space 17, microwave reflectors 18, 19, which are permeable to the fluid in the duct 14, form a resonant microwave cavity. A magnetron 22 provides microwave electromagnetic radiation into the cavity. Within the cavity are spheres 23, 24. The spheres 23, 24 may all comprise spherical electrodeless microwave lamps, in which case the fluid remediation zone of FIG. 1 operates to wholly or partially destroy microorganisms by means of ultraviolet radiation alone. On the other hand, in accordance with the invention, the spheres 23 may comprise spherical electrodeless ultraviolet lamps and the spheres 24 may be non-lamp spheres having an ultraviolet-activated photocatalyst surfaces, in which case the fluid remediation zone of FIG. 1 utilizes photocatalyst reaction with the fluid to remediate the fluid in some fashion, such as to oxidize or reduce organic compounds within the fluid. The spheres 23, 24 may instead comprise spherical electrodeless ultraviolet lamps having a photocatalytic coating thereon, the coating being sufficiently thin to be substantially transparent to microwave electromagnetic radiation, so the radiation can penetrate to the substance within the sphere thereby to maintain the ultraviolet radiation which activates the photocatalyst on the surface of the spheres 23, 24. The thickness of the coating can be determined from U.S. Pat. No. 5,865,959. In this case, there is a photocatalytic reaction with material in the fluid. In FIG. 1, instead of spheres 24, the spherical electrodeless ultraviolet lamps 23 may have particles interspersed therewith, the particles either being of a photocatalyst material, or being of a non-photocatalyst material but having a photocatalyst coating thereon. In FIG. 1, if desired, the microwave reflectors 18, 19 may be coated with a photocatalyst so as to enhance the interaction with the fluid.

In FIG. 2, a fluid remediation zone 26 includes the duct 14, the microwave reflective surfaces 18, 19 and the magnetron 22, but instead of spheres, it contains cylindrical electrodeless ultraviolet lamps 27. The lamps 27 are disposed with their axes of symmetry parallel to the long dimension of the duct so that fluid can flow within the interstices therebetween, but any possible angle between the cylinder axis and the duct flow is acceptable. The lamps 27 may be coated with an appropriately thin layer of ultraviolet-activated photocatalyst. In FIG. 2, the cylindrical electrodeless ultraviolet lamps 27 may have particles (e.g., spheres, cylinders, or any geometry) interspersed therewith, the particles either being of a photocatalyst material, or being of a non-photocatalyst material but having a photocatalyst coating thereon.

In FIG. 3, a remediation zone 30 comprises the duct 14 and magnetron 22, with a plurality of permeable substrates 31–33 with cylindrical electrodeless ultraviolet lamps disposed therebetween. At least the end substrates 33 (the other not shown) must be microwave-reflecting material so as to form a microwave cavity within the duct 14. All of the substrates 31–33 are provided with a photocatalytic surface which, when activated by radiation from the lamps 36, will cause chemical reactions with material (typically hydrocarbons) in the fluid, to oxidize or reduce such materials in order to affect them in a desired way, such as to render them harmless.

Instead of being energized through cavity resonance as in FIGS. 1–3, the tubes 36 may be activated as in FIG. 4 by radio frequency (RF) electromagnetic radiation inductively coupled from an RF power supply 39 by coils 40. The power supply 39 may have coils 40 for each of the tubes, or each tube may have its own power supply, as suits any implementation of the present invention. On the other hand, each of the tubes 36 may be disposed as in FIG. 5 within its own microwave cavity which is formed, with a magnetron 22, by suitable microwave reflective, permeable material 43 as shown in FIG. 5. The permeable substrates 31–33 and 43 may be any sort of labyrinth, mesh, net, screen or other perforated material which can both serve as an microwave mirror and allow adequate fluid to pass therethrough.

As used herein, the term "electrodeless ultraviolet lamp" means an ultraviolet lamp which can sustain ultraviolet radiation, without excitation by electrodes within the lamp, due to microwave or RF excitation, but includes lamps in which electrodes are provided in order to assist in commencement of the ultraviolet discharge, as illustrated by the electrodeless lamp 44 in FIG. 6. Therein, the lamp 44 has bases 45 in addition to the gas filled cylinder 46, there being electrodes 47 extending from each base into the cylinder 46. During ignition, a start-up power supply 48 temporarily provides electric power to the electrodes 47 so as to enhance the ultraviolet discharge within the cylinder 46, as the cylinder is irradiated with electromagnetic radiation, as described hereinbefore. However, electric power to the electrodes is shut off once ultraviolet radiation has been obtained, and the ultraviolet radiation is sustained solely by the electromagnetic radiation. In this way, the long-term heat effects, including generating deposits in the lamp, are avoided.

Emission of ultraviolet radiation is described in Boulos, M. I. et al, *Thermal Plasma: Fundamentals and Applications*, Vol. 1, Plenum Press, N.Y., 1944. Microwave driven electrodeless ultraviolet lamps are available from Fusion UV Systems, Inc. Inductively driven electrodeless ultraviolet lamps are available from Sylvania and from Phillips.

The aforementioned patents are incorporated herein by reference.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

We claim:

1. A fluid remediation zone, comprising:
a plurality of electrodeless ultraviolet lamps disposed in a finite space through which a stream of fluid may pass to be remedied;
means for exciting said electrodeless ultraviolet lamps with microwave electromagnetic radiation so that said lamps emit ultraviolet electromagnetic radiation within said space; and
a plurality of ultraviolet-activated photocatalyst surfaces disposed in said space so that said photocatalyst surfaces, when activated by said ultraviolet electromagnetic radiation, react with matter in said fluid to thereby remediate said fluid;
said surfaces being external surfaces of said lamps, said surfaces being sufficiently thin to be substantially transparent to microwave electromagnetic radiation.

2. A fluid remediation zone, comprising:
a plurality of electrodeless ultraviolet lamps disposed in a finite space through which a stream of fluid may pass to be remedied; and
means for exciting said electrodeless ultraviolet lamps with microwave electromagnetic radiation so that said lamps emit ultraviolet electromagnetic radiation within said space;
said electrodeless ultraviolet lamps comprise a plurality of spheres or cylinders arranged in said space to provide interstices therebetween through which said stream may pass, said lamps having a coating of ultraviolet-activated photocatalyst so that said photocatalyst when activated by said ultraviolet electromagnetic radiation, reacts with matter in said fluid to thereby remediate said fluid, said coating being sufficiently thin to be substantially transparent to said microwave electromagnetic radiation.

3. A fluid remediation zone according to claim 1 or claim 2 wherein:
said ultraviolet electromagnetic radiation interacts with contaminants in said stream of fluid to decontaminate said stream of fluid.

4. A fluid remediation zone according to claim 1 or claim 2 wherein:
said space is confined by a microwave-reflecting material, thereby forming a microwave cavity, at least one portion of said cavity being permeable to said fluid; and
said means comprises a magnetron disposed to emit microwave electromagnetic radiation into said cavity.

5. A fluid remediation zone according to claim 1 or claim 2 wherein said means comprises:
a plurality of magnetrons, one for each of said lamps;
a plurality of cavities, one far each of said lamps, each formed with a corresponding one of said magnetrons and with microwave reflecting porous material which is permeable by said fluid.

6. A fluid remediation zone, comprising:
a plurality of spherical electrodeless ultraviolet lamps disposed in a finite space in mutual contact with each other forming a bed having interstices between said lamps through which a fluid may pass to be remediated; and
means for exciting said electrodeless ultraviolet lamps with electromagnetic radiation so that said lamps emit ultraviolet electromagnetic radiation throughout said space.

7. A fluid remediation zone, comprising:
a plurality of electrodeless ultraviolet lamps and a plurality of particles of ultraviolet-activated photocatalyst disposed in an intermingled fashion, filling a finite space through which a fluid stream may pass to be remediated, each of said lamps in mutual contact with other ones of said lamps and/or said particles, and each of said particles in mutual contact with other ones of said particles and/or said lamps, forming a bed of particles and lamps having interstices therebetween through which said fluid may pass; and
means for exciting said lamps with electromagnetic radiation so that said lamps emit ultraviolet radiation within said space to thereby activate said particles throughout said space.

* * * * *